(12) United States Patent
Szakelyhidi

(10) Patent No.: US 9,634,393 B2
(45) Date of Patent: Apr. 25, 2017

(54) ANTENNA SYSTEM FOR SIGNAL-ATTENUATING CONTAINERS

(71) Applicant: Physio-Control, Inc., Redmond, WA (US)

(72) Inventor: David C. Szakelyhidi, Issaquah, WA (US)

(*) Notice: Subject to any disclaimer, the term of this patent is extended or adjusted under 35 U.S.C. 154(b) by 0 days.

(21) Appl. No.: 15/238,564

(22) Filed: Aug. 16, 2016

(65) Prior Publication Data

US 2016/0359233 A1    Dec. 8, 2016

Related U.S. Application Data

(60) Continuation of application No. 14/864,444, filed on Sep. 24, 2015, which is a division of application No. 14/090,824, filed on Nov. 26, 2013, now Pat. No. 9,172,129.

(51) Int. Cl.
| | |
|---|---|
| *H01Q 9/04* | (2006.01) |
| *H01Q 1/42* | (2006.01) |
| *H01Q 1/48* | (2006.01) |
| *H01Q 1/24* | (2006.01) |
| *H01Q 1/32* | (2006.01) |

(52) U.S. Cl.
CPC ............ *H01Q 9/0407* (2013.01); *H01Q 1/24* (2013.01); *H01Q 1/3291* (2013.01); *H01Q 1/42* (2013.01); *H01Q 1/48* (2013.01)

(58) Field of Classification Search
CPC ...... H01Q 1/22; H01Q 1/2208; H01Q 9/0407; A61N 1/3968; A61N 1/37229
See application file for complete search history.

(56) References Cited

U.S. PATENT DOCUMENTS

| | | | |
|---|---|---|---|
| 2006/0149321 A1 | 7/2006 | Merry et al. | |
| 2007/0205946 A1* | 9/2007 | Buris | H01Q 1/007 343/700 MS |
| 2012/0098664 A1* | 4/2012 | Nordin | G06K 7/0008 340/572.1 |

* cited by examiner

*Primary Examiner* — Rex R Holmes
(74) *Attorney, Agent, or Firm* — Baker & Hostetler LLP

(57) ABSTRACT

A system can include a container that includes a cabinet capable of attenuating or blocking wireless signals, an AED located within the cabinet, an internal patch antenna removably mounted to an internal surface of the cabinet, an external patch antenna removably mounted to an external surface of the cabinet, and an electrical connection between the internal patch antenna and the external patch antenna. The internal and external patch antennas can be configured to transmit wireless signals at a particular frequency and to receive wireless signals at the particular frequency. The system can be configured such that the internal patch antenna is operative to receive a first wireless signal from the AED, a first electrical signal based on the first wireless signal is provided via the electrical connection to the external patch antenna, and a second wireless signal based on the first electrical signal is radiated by the external patch antenna.

9 Claims, 12 Drawing Sheets

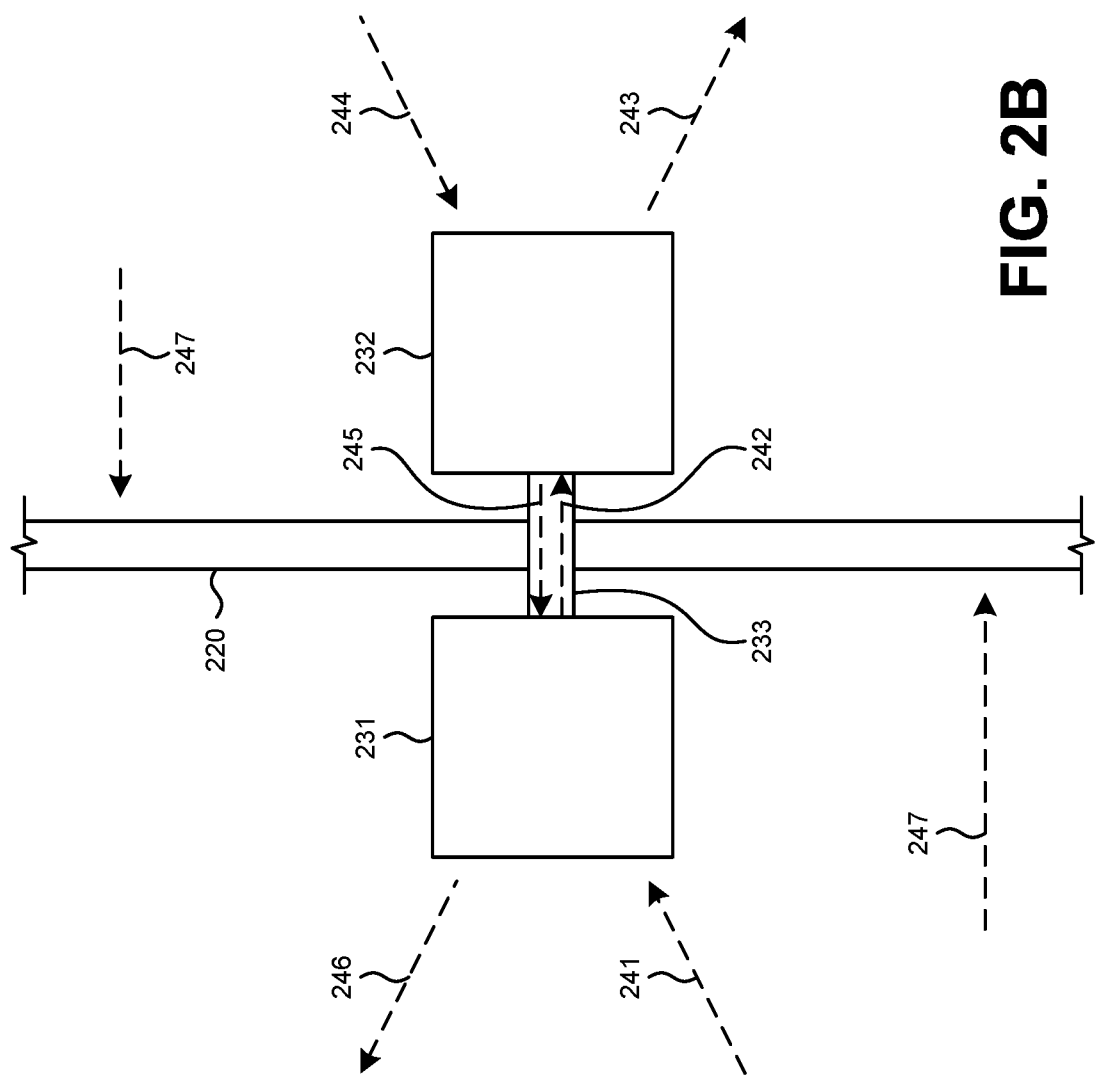

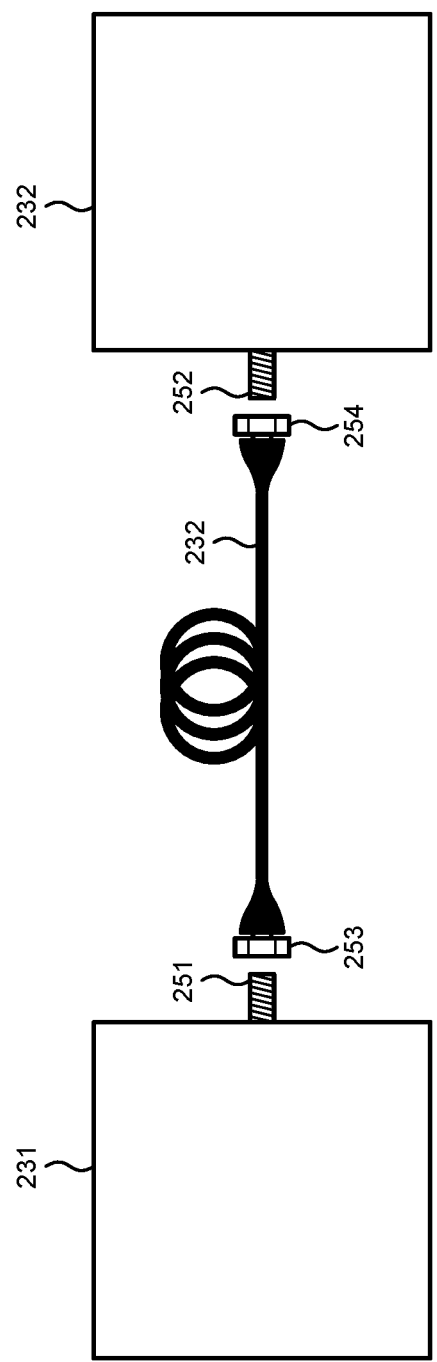

ANTENNA SYSTEM FOR SIGNAL-ATTENUATING CONTAINERS

CROSS REFERENCE TO RELATED APPLICATIONS

This application is a continuation of U.S. patent application Ser. No. 14/864,444 filed Sep. 24, 2015, entitled "ANTENNA SYSTEM FOR SIGNAL-ATTENUATING CONTAINERS," which is a divisional of U.S. patent application Ser. No. 14/090,824 filed Nov. 26, 2013, entitled "ANTENNA SYSTEM FOR SIGNAL-ATTENUATING CONTAINERS," (now U.S. Pat. No. 9,172,129 issued Oct. 27, 2015), the contents of each are hereby incorporated by reference in its entirety.

BACKGROUND

An automated external defibrillator (AED) is a portable electronic device that treats cardiac arrhythmias through defibrillation. Such cardiac arrhythmias are potentially life-threatening and the sooner that an AED can be used to treat a patient, the greater the likelihood that the defibrillation by the AED will benefit the patient. Defibrillation by an AED can include the application of electrical therapy which stops the arrhythmia and allows the heart to reestablish an effective rhythm. Some AEDs can automatically diagnose arrhythmias and tailor patient treatment to meet the diagnosis. AEDs are typically designed so that someone without extensive medical training can effectively use AEDs to provide defibrillation treatment, though many AED training programs are available for basic training on how to use an AED.

Because patients typically benefit from administering AED treatment sooner, many public places, such as libraries, movie theaters, hotels, high-rise buildings, and the like, are placing AEDs in accessible locations. While public places may want to make AEDs accessible, they also want to ensure that AEDs are protected from inadvertent, unintended, or nefarious use, such as use by a child, by a vandal, and the like. To protect AEDs while making them available for use, AEDs are frequently placed inside of protective containers, such as metal cabinets or containers. Other devices, such as fire extinguishers, are similarly placed in protective containers to prevent unwanted uses of the devices while making the devices readily available for use.

SUMMARY

Illustrative embodiments of the present invention include, without limitation, methods, structures, and systems. In one embodiment, a system can include a container that includes a metal cabinet, an AED located within the metal cabinet, an internal patch antenna removably mounted to an internal surface of the metal cabinet, an external patch antenna removably mounted to an external surface of the metal cabinet, and an electrical connection between the internal patch antenna and the external patch antenna. The AED can be configured to communicate, via wireless signals at one or more particular frequencies, with other devices or networks. Such communication to and from the AED can used for a number of purposes, such as AED software updates, query of AED state or errors, AED event data transmission, or remaining shelf life of time sensitive components of the AED. The internal patch antenna can be configured to transmit wireless signals at the one or more particular frequencies and to receive wireless signals at the one or more particular frequencies. The external patch antenna can be configured to transmit wireless signals at the one or more particular frequencies and to receive wireless signals at the one or more particular frequencies. The system can be configured such that the internal patch antenna is operative to receive a first wireless signal from the AED, a first electrical signal based on the first wireless signal is provided via the electrical connection to the external patch antenna, and a second wireless signal based on the first electrical signal is radiated by the external patch antenna.

In one example, the system can be further configured such that the external patch antenna is operative to receive a third wireless signal, a second electrical signal based on the third wireless signal is provided via the electrical connection to the internal patch antenna, and a fourth wireless signal based on the second electrical signal is radiated from the internal patch antenna. In other examples, the metal cabinet can include a door and a doorway. The electrical connection can be routed through the doorway. The electrical connection can include a ribbon cable. The electrical connection can be routed through a hinge area of the doorway. The electrical connection can be routed through a hole in the metal cabinet.

In another embodiment, a system can include a container, a device located within the container, an internal patch antenna removably mounted to an internal surface of the container, an external patch antenna removably mounted to an external surface of the container, and an electrical connection between the internal patch antenna and coupled to the external patch antenna. The device can be configured to communicate wireless signals at one or more particular frequencies. The internal patch antenna can be configured to transmit wireless signals at the one or more particular frequencies and to receive wireless signals at the one or more particular frequencies. The external patch antenna can be configured to transmit wireless signals at the one or more particular frequencies and to receive wireless signals at the one or more particular frequencies. The system can be configured such that the internal patch antenna is operative to receive a first wireless signal from the device, a first electrical signal based on the first wireless signal is provided via the electrical connection to the external patch antenna, and a second wireless signal based on the first electrical signal is radiated by the external patch antenna.

In one example, the system can be further configured such that the external patch antenna is operative to receive a third wireless signal, a second electrical signal based on the third wireless signal is provided via the electrical connection to the internal patch antenna, and a fourth wireless signal based on the second electrical signal is radiated from the internal patch antenna. In other examples, the one or more frequencies can include at least one of a cellular network frequency, a Wi-Fi frequency, or an RFID tag frequency. The one or more frequencies can include a plurality of frequencies. The device can be configured to communicate wireless signals at the one or more particular frequencies by transmitting an RFID signal from an RFID tag. The container can include at least one of a cabinet, a storage room, a vehicle trunk, a vehicle compartment, an elevator, a subway compartment, a train compartment, an aircraft compartment, or a vehicle.

In another embodiment, an apparatus can include a first patch antenna, a second patch antenna, and an electrical connection between the first patch antenna and the second patch antenna. The first patch antenna can be configured to transmit wireless signals at one or more particular frequencies and to receive wireless signals at the one or more particular frequencies. The second patch antenna can be configured to transmit wireless signals at the one or more particular frequencies and to receive wireless signals at the one or more particular frequencies. Each of the first patch antenna and the second patch antenna can include a ground plane, a spacer disposed on the ground plane where the spacer includes a magnetic material, and a patch disposed on the spacer.

The present invention is not limited to any specific design or configuration of patch antennae. In view of the present disclosure, those of skill in the art will appreciate that a patch antenna is a type of radio antenna with a low profile suited for mounting on a flat surface. A patch antenna typically includes a flat rectangular sheet of metal mounted over a larger sheet of metal called a ground plane. The assembly can be contained inside a plastic radome, which protects the antenna structure from damage. Patch antennas are suited to be used in the illustrative embodiments of the present invention since they are easy to fabricate and modify for a particular application. The two metal sheets together form a resonant microstrip transmission line with a length of approximately one-half wavelength. A patch antenna is usually constructed on a dielectric substrate, using the same materials and lithography processes used to make printed circuit boards.

BRIEF DESCRIPTION OF THE DRAWINGS

Throughout the drawings, reference numbers may be re-used to indicate correspondence between referenced elements. The drawings are provided to illustrate example embodiments described herein and are not intended to limit the scope of the disclosure.

FIGS. 2A to 2D depict a system that increases the ability of a device in a container to communicate wirelessly with a device or network outside of the container.

DETAILED DESCRIPTION OF ILLUSTRATIVE EMBODIMENTS

Figure 1:
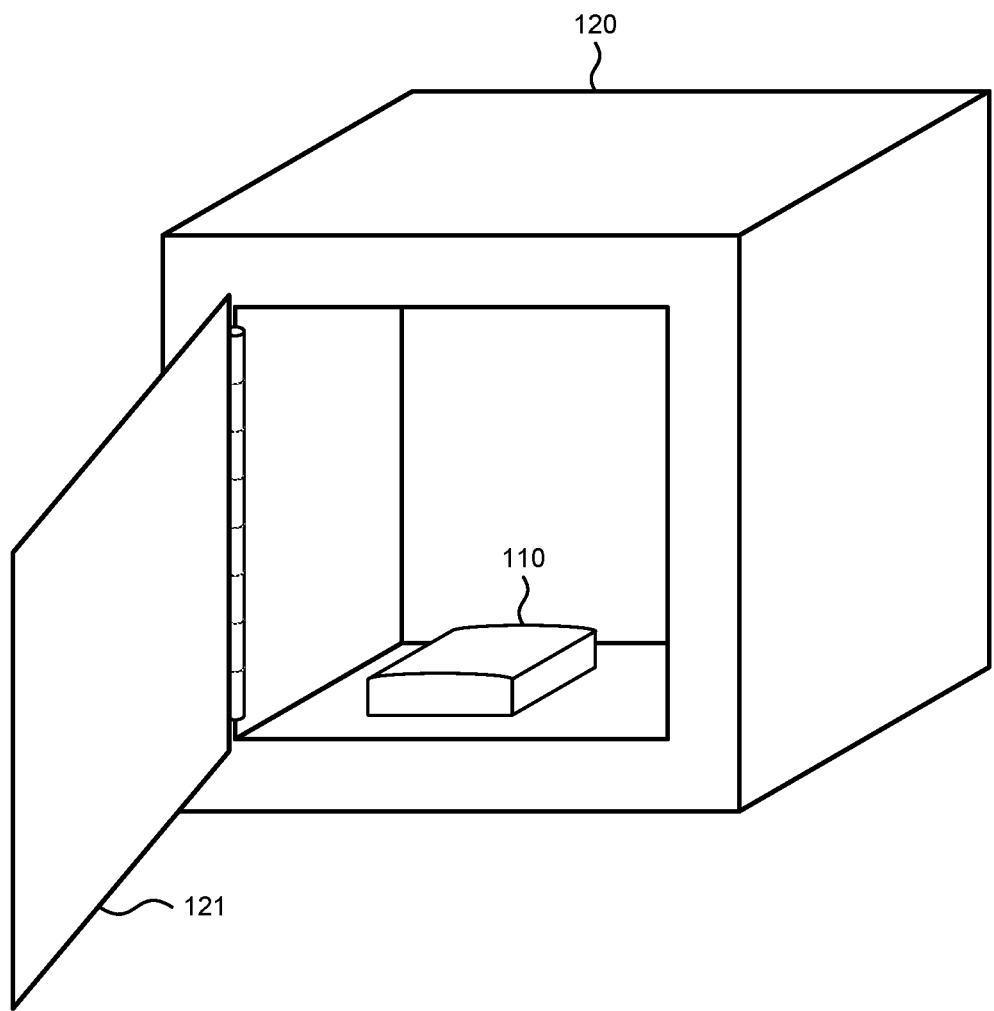
FIG. 1 depicts an example of a device that is stored in a container.

FIG. 1 depicts an example of a device 110 that is stored in a container 120. The container 120 can be a cabinet, such as a metal cabinet, as depicted in FIG. 1. The container 120 can take a number of other forms, such as a storage room, a vehicle trunk, a vehicle compartment, an elevator, a subway compartment, a train compartment, an aircraft compartment, a vehicle, and the like. The container 120 can include a door 121. The door 121 depicted in FIG. 1 is a hinged door, though many other types of doors could be used. The door 121 can be a solid material, such as metal, or a combination of materials, such as a metal frame with a plastic or glass window.

Devices stored in containers increasingly have a need to communicate wirelessly with communication devices that are outside of the containers. For example, some AEDs may be able to communicate via a WiFi, cellular, RFID, or other wireless network to provide notifications device location, software updates or query of device state or errors (collectively referred to as "readiness data"), information about device event data, information about remaining shelf life of time sensitive device components, or any other type of information. In another example, some fire extinguisher devices may be able to communicate via a wireless network to provide information similar to those types of information described above with respect to the AED above.

In another example, a device inside of a container may have a radio frequency indentation (RFID) tag that can be used for asset tracking. In this scenario, the RFID tag on the device may transmit a radio signal that can identify the tag and a tracking device may receive the signal and identify that the particular device is within range of the tracking device. For example, a tracking device may be placed inside of a room at a hospital and read all RFID signals from RFID tags that are associated with equipment in the room. The tracking device may record all the devices determined to be in the room, and those devices can be tracked without a user needing to visually identify each of the devices. Avoiding the need to visually identify each device can be helpful, especially when one or more devices are stored in one or more containers.

One difficulty with devices stored in containers communicating wirelessly is that the containers may block wireless signals or attenuate signal strength of wireless signals. By attenuating or blocking wireless signals, containers can make wireless communication between a device inside of the container with a device or network outside of the container difficult or impossible.

FIGS. 2A-2D depict a system that increases the ability of a device 210 in a container 220 to communicate wirelessly with a device or network outside of the container. The system also includes an antenna system 230 that includes an internal patch antenna 231 and an external patch antenna 232. Each of the internal patch antenna 231 and the external patch antenna 232 can be tuned to one or more target frequencies. A patch antenna is tuned to a target frequency when it is capable of sending and receiving wireless signals at or near that target frequency. Particular frequencies that may be target frequencies include frequencies that are used by cellular networks, such as 850 MHz, 900 MHz, 1,800 MHz, or 1,900 MHz, frequencies that are used by Wi-Fi networks, such as 2.4 GHz, and frequencies used by FRID tags, such as 120-150 kHz, 13.56 MHz, 433 MHz, 865-868 MHz, 902-928 MHz, 2450-5800 MHz, or 3.1-10 GHz. In one embodiment, each of the internal patch antenna 231 and the external patch antenna 232 can be tuned to one or more of a cellular network frequency, a Wi-Fi frequency, or an RFID tag frequency. In some embodiments, a device with wireless communication capability can be provided with the antenna system 230 so that a user or installer can upgrade or retrofit a previously installed container to enhance the ability of the device to wirelessly communicate with devices or networks outside of the container. For example, when replacing an older AED that does not communicate wirelessly with a new AED that does communicate wirelessly, the new AED may be placed in the same cabinet as the old AED. However, since the old AED did not have the ability to communicate wirelessly, a patch antenna system could be installed on the cabinet at the time that the new AED is installed. In this case, it may be helpful for the patch antenna system to be provided as a kit with the new AED.

The internal patch antenna 231 and the external patch antenna 232 can be removably mounted to one of the sides of the container 220. A patch antenna is removably mounted to the container if it is mounted to the container in a way that is easily removed, such as using a magnetic mounting, an adhesive mounting that permits the patch antenna to be peeled off of the container by hand, a hook and loop mounting, or similar mounting. A patch antenna is not removably mounted to the container if it is mounted to the container using screws, rivets, bolts, or other similar fasteners, or if the patch antenna is permanently affixed to the container, such as if it is welded to the container.

The internal patch antenna 231 and the external patch antenna 232 are connected via an electrical connection 233. The electrical connection can be a low profile ribbon cable, a flexible trace, a coaxial cable, or any other type of electrical connection that can carry signals between the internal patch antenna 231 and the external patch antenna 232. Such alternative types of electrical connections may also include those which are non-contact in nature. An example of non-contact electrical connection between antennas could include inductive and capacitive coupling, where the electrical signals are passed across/through the wall of the container. Conductors are referred to as mutual-inductively coupled or magnetically coupled when they are configured such that change in current flow through one wire induces a voltage across the ends of the other wire through electromagnetic induction. In such an embodiment, the wall of the container residing between the internal and external antennas, regardless of metal composition type, can be factored as a component in the proper tuning and matching of the non-contact electrical connection.

FIG. 2B depicts the passing of signals inside of the container 220, outside of the container 220, and between the inside and the outside of the container 220. The internal patch antenna 231 can receive a first wireless signal 241, the internal patch antenna 231 can send a first electrical signal 242 to the external patch antenna 232 via the electrical connection 233, and the external patch antenna 232 can transmit a second wireless signal 243 outside of the container 220. The second wireless signal 243 can be a continuation of the first wireless signal 241, though some losses could be incurred in the antenna system 230. The information carried by the first wireless signal 241 is also carried in the second wireless signal 243. Similarly, the external patch antenna 232 can receive a third wireless signal 244 from outside the container 220, the external patch antenna 232 can send a second electrical signal 245 to the internal patch antenna 231 via the electrical connection 233, and the internal patch antenna 231 can transmit a fourth wireless signal 246 inside of the container 220. The fourth wireless signal 246 can be a continuation of the third wireless signal 244, though some losses could be incurred by the antenna system 230.

Figure 2A:
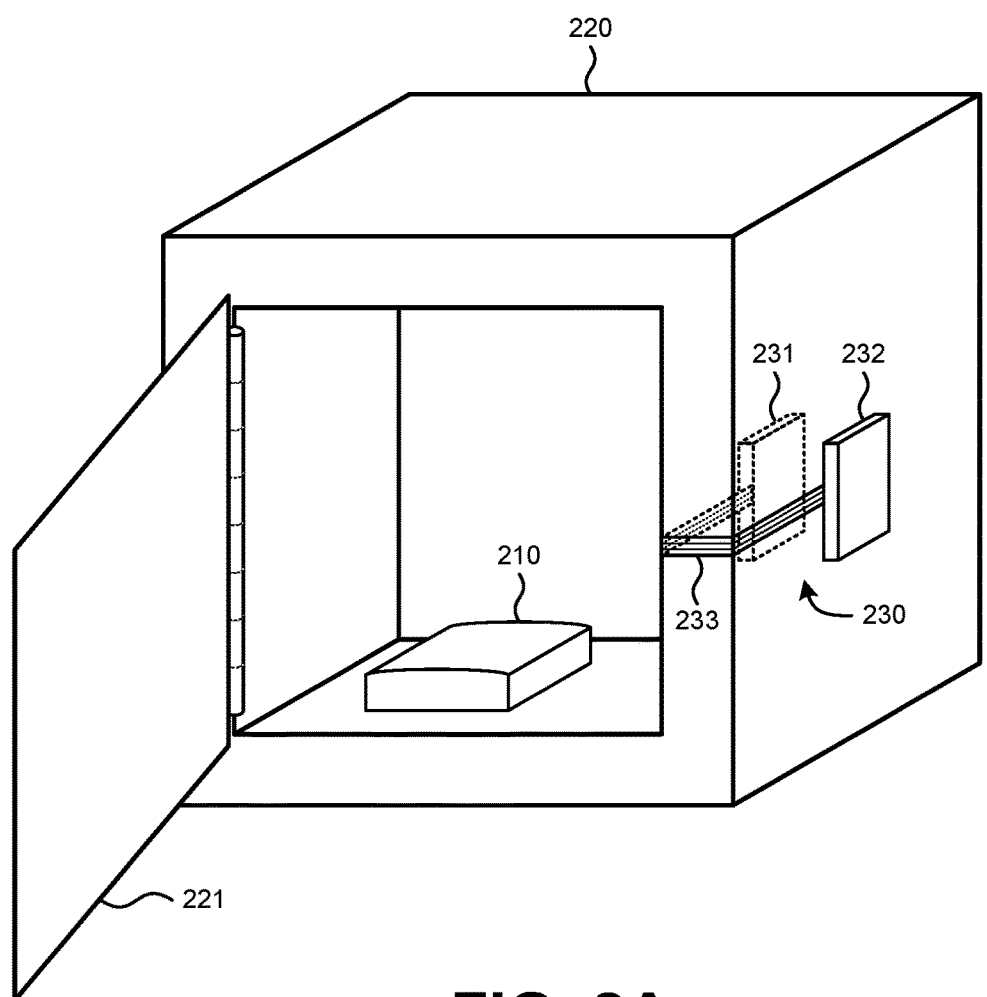
Figure 2C:
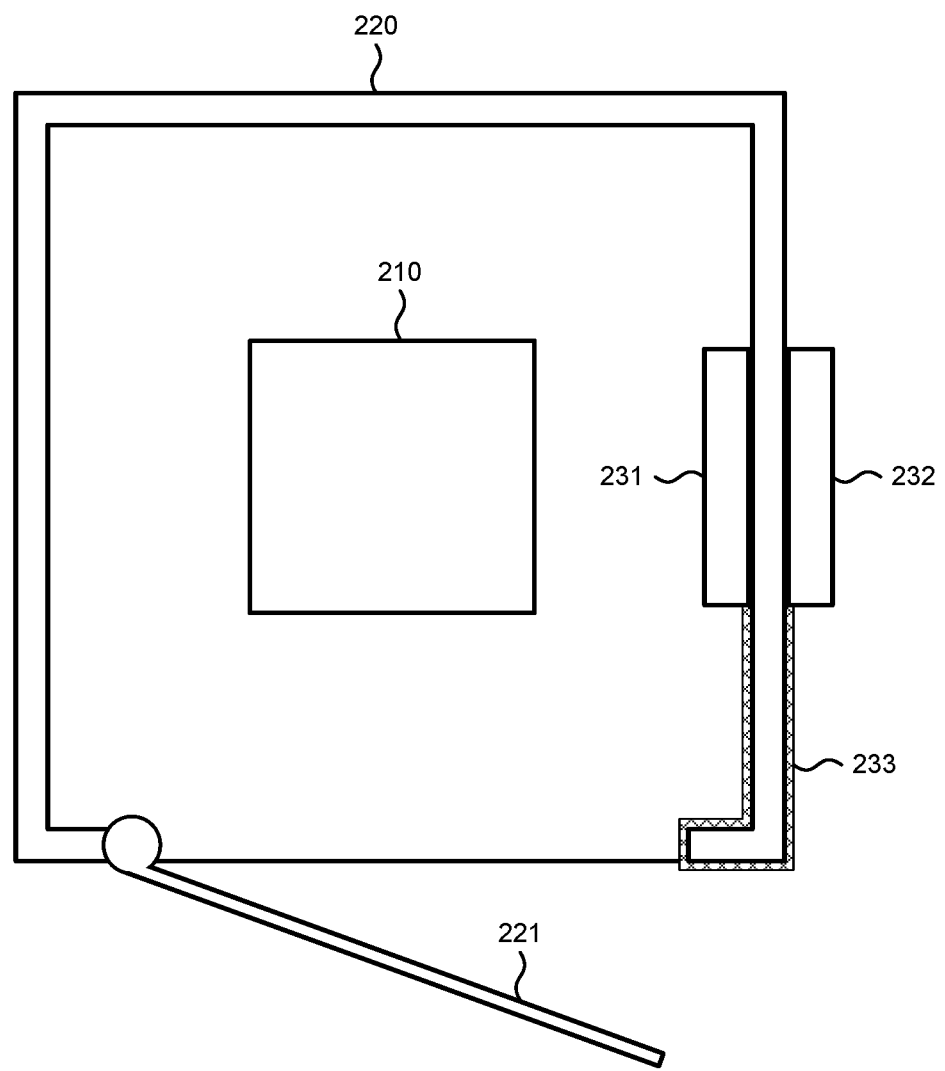

The size and shape of the electrical connection 233 can be selected based on how the electrical connection 233 is fed between the internal patch antenna 231 and the external patch antenna 232. FIG. 2C depicts a cross-sectional view of the embodiment shown in FIG. 2A looking down from the top of the container 220. In the embodiment depicted in FIGS. 2A and 2C, the electrical connection 233 is fed through the opening in the container 220 that can be covered by the door 221. In this case, a thin ribbon cable can be used as the electrical connection 233 without having a significantly adverse effect on the closing of the door 221. While a ribbon cable may not permit the door 221 to fully close, the ribbon cable may still allow the door 221 to latch. In this way, the antenna system 230 can be installed on an existing container without a need for tools to cut a hole in the container 220 and so forth. The electrical connection 233 could also be similarly fed through a hinge area of the container 220, a door seal between the container 220 and the door 221, any small passage or crack in the container 220, or any other access point.

FIG. 2D depicts an example of connecting electrical connection 232 between the internal patch antenna 231 and the external patch antenna 232. The internal patch antenna 231 can include a connector 251 and the external patch antenna 232 can include a connector 252. One end of the electrical connection 233 cable can include a mating connector 253 and the other end of the electrical connection 233 can include a mating connector 254. In this way, the electrical connection 233 can be easily disconnected from the internal patch antenna 231 and the external patch antenna 232, and a length of the electrical connection 233 can be determined based on the appropriate scenario in which the internal patch antenna 231 and the external patch antenna 232 will be placed.

Other shapes and sizes of the electrical connection 233 could be used. In the example shown in FIG. 2D, the electrical connection 233 is in the form of a coaxial cable. A coaxial cable may be beneficial in a scenario where a hole exists in a side of the container 220. Alternatively, a hole in the container for the electrical connection 233 could be drilled. The container could also have a pre-scored hole that an end user can punch out with a screwdriver or similar tool should the end user want to feed the electrical connection 233 through such a hole.

Figure 3A:
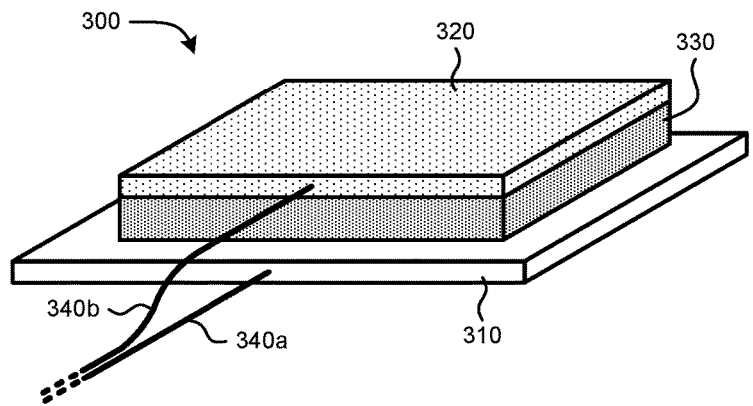
FIGS. 3A to 3C depict views of an example patch antenna.
Figure 3B:
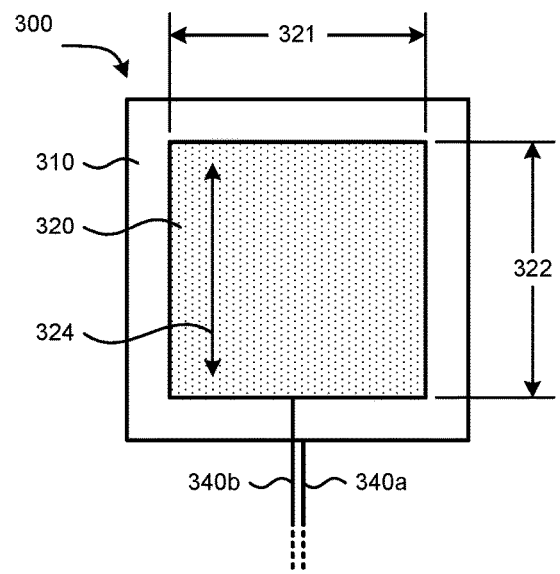
Figure 3C:
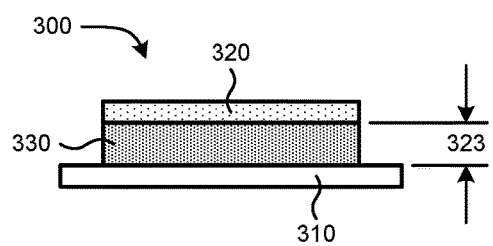

FIGS. 3A to 3C depict views of an example of a patch antenna 300 that can be used to implement an internal patch antenna such as internal patch antenna 231 and/or an external patch antenna such as external patch antenna 232 depicted in FIGS. 2A-2D. The patch antenna 300 includes a ground plane 310 and a patch 320. A spacer 330 can be placed between the ground plane 310 and the patch 320. The spacer can be made out of a dielectric material or an electrically insulative material. Typically, the ground plane 310 is larger in size than the patch 320. The patch 320 can have particular dimensions, such as a width 321 and a height 322. The ground plane 310 and the patch 320 can be held apart at a distance 323 from each other. Electrical leads 340 can be connected to the ground plane 310 or the patch 320. In the particular embodiment shown in FIGS. 3A to 3C, one electrical lead 340a is coupled to the ground plane 310 and another electrical lead 340b is coupled to the patch 320. While one electrical lead is coupled to each of the ground plane 310 and the patch 320 in the depiction of FIGS. 3A to 3C, more than one electrical leads could be coupled to one or both of the ground plane 310 and the patch 320.

The shape of the patch 320, the dimensions of the patch 320, and the distance between the ground plane 310 and the patch 320 can be selected so that the ground plane 310 and the patch 320 resonate at particular frequencies. In one embodiment, the height 322 of the patch is selected to be one half of the wavelength of a target frequency. The ground plane 310 and the patch 320 can radiate due to discontinuities at each truncated edge of a microstrip transmission line. The ground plane 310 can be constructed on a dielectric substrate, using materials and lithography processes similar to those used to make printed circuit boards. When the ground plane 310 is close to the size of the patch 320, it can couple and produce currents along the edges of the ground plane which also radiate. The current flow is along the direction of the arrow 324 shown in FIG. 3B, so the magnetic vector potential and thus the electric field follow the current. A patch antenna 300 can radiate a linearly polarized wave.

Patch antenna 300 can be fabricated by etching a pattern for the patch 320 in metal trace bonded to an insulating dielectric substrate, such as a printed circuit board, with a continuous metal layer bonded to the opposite side of the substrate which forms the ground plane 310. While the shape of the patch 320 shown in FIGS. 3A to 3C is square, other shapes can be used such as rectangular, circular, and elliptical shapes.

In one embodiment, the spacer 330 can be formed of a magnetic material. In this way, the magnetic material of the spacer can sever both the function of the spacer for the patch antenna 300 and as a mechanism for removably mounting the patch antenna 300 to a magnetic surface. The magnetic material can be flexible, and the materials for the ground plane 310 and the patch 320 can also be flexible. In this manner, the entire patch antenna 300 can be flexible. Such a low-profile, magnetic antenna can be removably mounted to a number of magnetic surfaces, such as a side of a metal cabinet, a curved metallic surface, and so forth.

FIGS. 4A to 4D depict various embodiments of patch antennas 400 that can be used to implement an internal patch antenna such as internal patch antenna 231 and/or an external patch antenna such as external patch antenna 232 depicted in FIGS. 2A-2D. Each of the patch antennas 400 shown in FIGS. 4A to 4D includes a patch 402 that has a different shape. Various shapes of patches can be used for different reasons. For example, a particular shape of a patch can tune the patch antenna to receive and send signals at a particular frequency. In another example, a particular shape of a patch can tune the patch antenna to receive and send signals at a number of particular frequencies. It is possible that a certain implementation could require antenna shapes or dimensions that are at odds with the approach of antenna tuning by way of geometric component dimensional adjustment. In such cases, an appropriate combination of discrete electronic components (e.g., resistors, capacitors, inductors, etc.) can be used to alternatively achieve desired antenna tuning and characteristics.

Figure 4B:
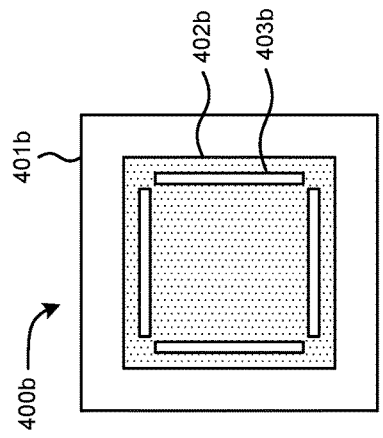
FIGS. 4A to 4D depict various embodiments of patch antennas.
Figure 4D:
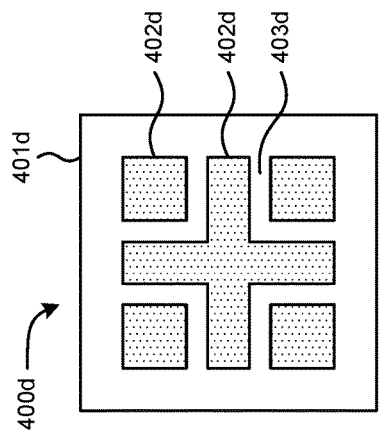
Figure 4A:
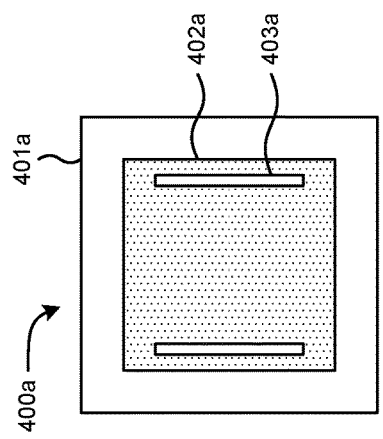
Figure 4C:
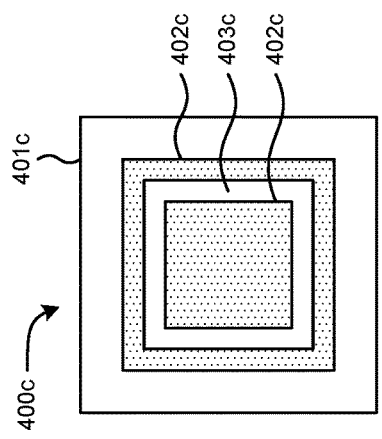

FIG. 4A depicts a patch antenna 400a that includes a backplane 401a and a patch 402a. The patch 402a includes slots 403a. The particular slots 403a in FIG. 4A include a pair of parallel slots. FIG. 4B depicts a patch antenna 400b that includes a backplane 401b and a patch 402b. The patch 402b includes slots 403b. The particular slots 403b in FIG. 4B include two pairs of parallel slots, with one of the pairs of parallel slots being substantially parallel to the other pair of parallel slots. FIG. 4C depicts a patch antenna 400c that includes a backplane 401c and a patch 402c. The patch 402c is formed in two pieces, with a central rectangle and an outer rectangular loop. The patch 402c also includes a slot 403c that is formed as a rectangular loop in the area between the two pieces of the patch 402c. In this scenario, for an electrical lead to be coupled to the patch 402c, the electrical lead may be coupled to both of the two pieces of the patch 402c. FIG. 4D depicts a patch antenna 400d that includes a backplane 401d and a patch 402d. The patch 402d is formed in five pieces, with a central plus-shaped piece and four rectangle pieces in the four quadrants of the plus-shaped piece. The patch 402d also includes slots 403c that are formed in the areas between the plus-shaped piece and the rectangular pieces of the patch 402d. In this scenario, for an electrical lead to be coupled to the patch 402d, the electrical lead may be coupled to more than one of the pieces of the patch 402d. Beyond those shapes depicted in FIG. 4A to 4D, many other possible shapes and sizes of patches are possible.

Figure 5A:
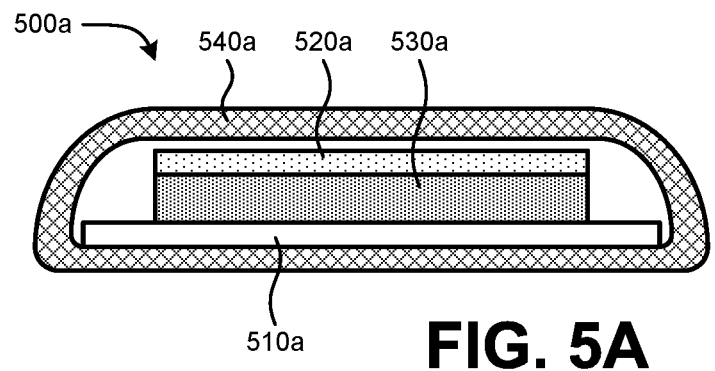
FIGS. 5A to 5C depict examples of cross sections of patch antennas that include protective coverings.
Figure 5B:
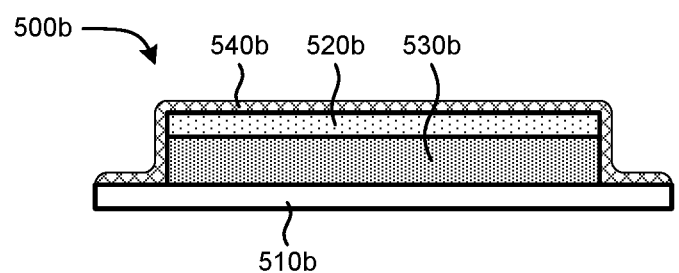
Figure 5C:
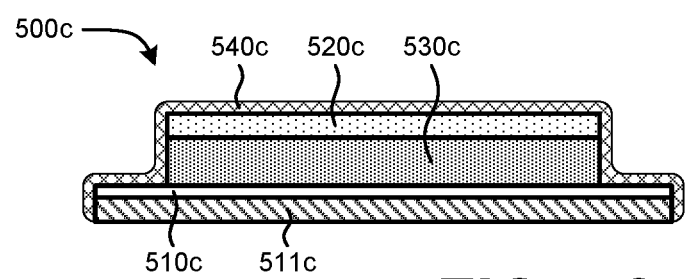

FIGS. 5A to 5C depict examples of cross sections of patch antennas 500 that include protective coverings that can be used to implement an internal patch antenna such as internal patch antenna 231 and/or an external patch antenna such as external patch antenna 232 depicted in FIGS. 2A-2D. FIG. 5A depicts a patch antenna 500a that includes ground plane 510a, a patch 520a, and a spacer 530a. The patch antenna 500a can also include a housing 540a that encases the ground plane 510a, the patch 520a, and the spacer 530a. The housing 540a, sometimes referred to as a radome, can be made of any material, such as plastic or ceramic, that does not substantially interfere with radio signals passing from outside the housing 540a to the ground plane 510a, the patch 520a, and the spacer 530a. A mechanism or material—such as a magnet, an adhesive material, a hook-and-loop material, and the like—for removably mounting the patch antenna 500a to a surface can be placed on the outside or inside of the housing 540a. In one embodiment, the material for removably mounting can be the spacer 530a if it is made from a magnetic material.

FIG. 5B depicts a patch antenna 500b that includes ground plane 510b, a patch 520b, and a spacer 530b. The patch antenna 500b can also include a protective layer 540b that covers portions of the ground plane 510b, the patch 520b, and the spacer 530b. The protective layer 540b can be a material, such as a plastic or a resin, that can be applied on the outside of the ground plane 510b, the patch 520b, and the spacer 530b in a liquid form and that can harden or cure to form the protective layer 540b. The protective layer 540b can also be a molded material, such as a soft plastic or rubber that is configured to cover the ground plane 510b, the patch 520b, and the spacer 530b. The protective layer 540b can protect the ground plane 510b, the patch 520b, and the spacer 530b from damage without substantially interfering with radio signals passing from outside the protective layer 540b to the ground plane 510b, the patch 520b, and the spacer 530b. In one embodiment, a mechanism or material for removably mounting the patch antenna 500b to a surface can be placed on the outside of the protective layer 540b or the outside of the ground plane 510b. In another embodiment, the spacer 530b can be made from a magnetic material to permit the patch antenna 500b to be removably mounted to a magnetic surface.

FIG. 5C depicts a patch antenna 500c that includes ground plane 510c, a patch 520c, and a spacer 530c. The ground plane 510c is located over a substrate 511c. In this embodiment, the ground plane 510c can be a very thin layer, such as a layer of metal foil. The substrate 511c can provide structural integrity and protection for the ground plane 510c. The patch antenna 500c can also include a protective layer 540c that covers portions of the ground plane 510b, the substrate 511c, the patch 520b, and the spacer 530b. The protective layer 540c can be similar to the protective layer 540b described above. The protective layer 540b can protect the ground plane 510c, the patch 520c, and the spacer 530c from damage without substantially interfering with radio signals passing from outside the protective layer 540c to the ground plane 510c, the patch 520c, and the spacer 530c. In one embodiment, a mechanism or material for removably mounting the patch antenna 500c to a surface can be placed on the outside of the protective layer 540c or the outside of the ground plane 510c. In another embodiment, the spacer 530c can be made from a magnetic material to permit the patch antenna 500c to be removably mounted to a magnetic surface.

Figure 6:
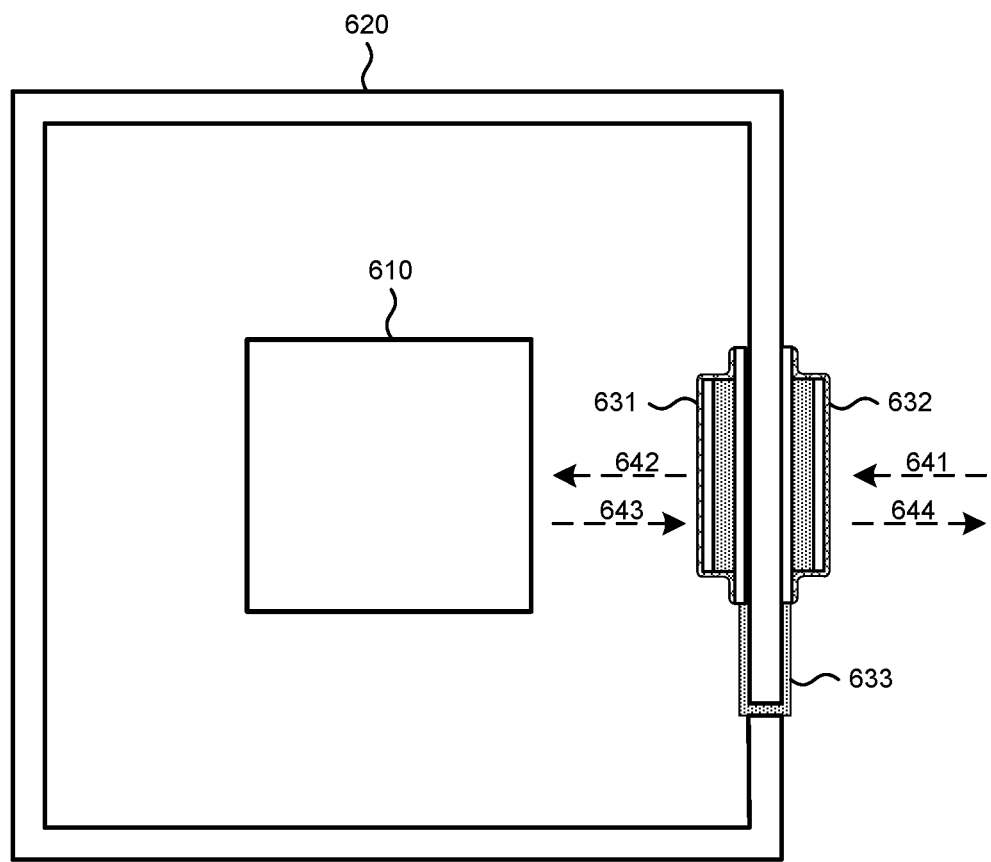
FIG. 6 depicts a cross-sectional view of an example of a container in which a device is stored.

FIG. 6 depicts a cross-sectional view of an example of a container 620 in which a device 610 is stored. The device 610 can be configured to communicate wirelessly using one or more of a Wi-Fi communication device, a cellular communication device, an RFID transmitter (either active or passive), and the like. The container 620 may block wireless signals or attenuate wireless signals to the point that wireless communication is difficult or impossible. FIG. 6 also depicts an internal patch antenna 631 and an external patch antenna 632. The internal patch antenna 631 and the external patch antenna 632 are depicted in a form that is similar to the patch antenna 500b depicted in FIG. 5B; however, the internal patch antenna 631 and the external patch antenna 632 can be in the form of the patch antenna 500a depicted in FIG. 5A, in the form of the patch antenna 500c depicted in FIG. 5C, or in any other form.

An electrical connection 633 is connected to both the internal patch antenna 631 and the external patch antenna 632. The electrical connection 633 is fed through a hole in the container 620. As discussed above, electrical leads of the electrical connection 633 can be coupled directly to portions of the internal patch antenna 631 and the external patch antenna 632, such as a ground plane or a patch of the internal patch antenna 631 and the external patch antenna 632. A directed coupling could be accomplished by soldering the electrical leads of the electrical connection 633, by welding the electrical leads of the electrical connection 633, or by any other like method. The electrical connection 633 can also be coupled to a connector of each of the internal patch antenna 631 and the external patch antenna 632. The electrical connection 633 can pass signals between the internal patch antenna 631 and the external patch antenna 632.

The internal patch antenna 631 and the external patch antenna 632 can be tuned to passively transmit and receive wireless signals at the same one or more target frequencies. For example, the external patch antenna 632 can receive a first wireless signal 641. The first wireless signal 641 can be at a particular frequency, such as 900 MHz, 1,800 MHz, 2.4 GHz, or any other frequency. The external patch antenna 632 can be tuned to receive wireless signals at the particular frequency and to send an electrical signal along the electrical connection 633 to the internal patch antenna 631. The internal patch antenna 631 can be tuned to transmit wireless signals at the particular frequency, and the internal patch antenna 631 can transmit a second wireless signal 642 at the particular frequency. The second wireless signal 642 can be similar to the first wireless signal 641, though some losses may be incurred between the receipt of the first wireless signal 641 by the external patch antenna 632 and the transmission of the second wireless signal 642 by the internal patch antenna 631. In another example, the internal patch antenna 631 can receive a third wireless signal 643 from the device 610. The third wireless signal 643 can be at a particular frequency, such as 900 MHz, 1,800 MHz, 2.4 GHz, or any other frequency. The frequency of the third wireless signal can be at the same frequency of the first wireless signal 641 or at a different frequency. The internal patch antenna 631 can be tuned to receive wireless signals at the particular frequency of the third wireless signal 643 and to send an electrical signal along the electrical connection 633 to the external patch antenna 632. The external patch antenna 632 can be tuned to transmit wireless signals at the particular frequency of the third wireless signal 643, and the external patch antenna 632 can transmit a fourth wireless signal 644 at the particular frequency of the third wireless signal 643. The fourth wireless signal 644 can be similar to the third wireless signal 643, though some losses may be incurred between the receipt of the third wireless signal 643 by the internal patch antenna 631 and the transmission of the fourth wireless signal 644 by the external patch antenna 632.

Figure 7A:
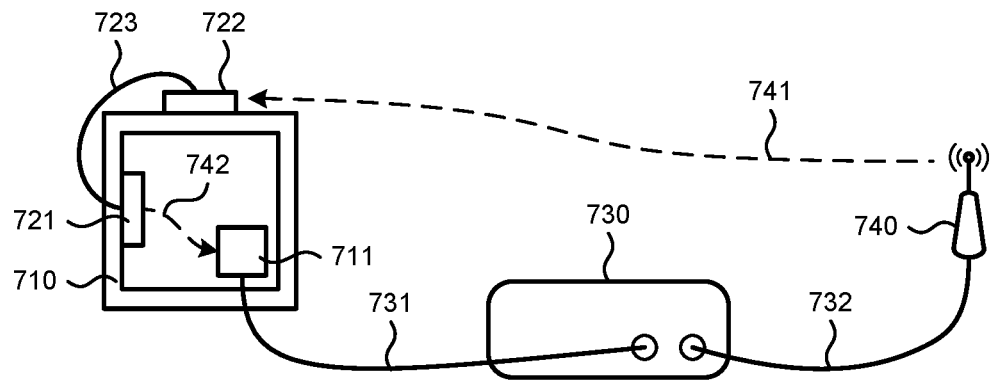
FIGS. 7A and 7B depict various testing arrangements for testing a patch antenna system.
Figure 7B:
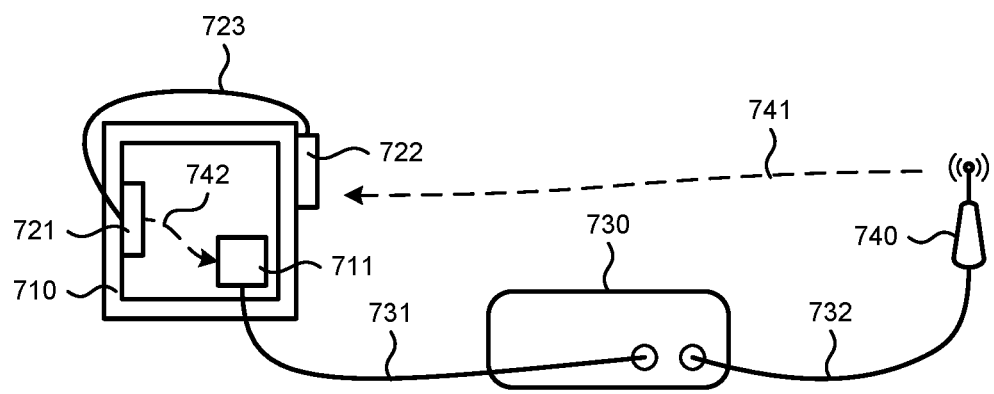

FIGS. 7A and 7B depict various testing arrangements for testing a patch antenna system. The testing arrangements include a container 710 and a wireless signal receiver 711 inside of the container. An internal patch antenna 721 is located inside of the container 710 and an external patch antenna 722 is located outside of the container 710. The internal patch antenna 721 and the external patch antenna 722 are coupled via an electrical connection 723. The testing arrangements include a network analyzer 730. A first electrical connection 731 is connected from a first port of the network analyzer 730 to the wireless signal receiver 711. A second electrical connection 732 is connected from a second port of the network analyzer 730 to a wireless transmitter 740. The wireless transmitter 740 is configured to emit a first wireless signal 741. The external patch antenna 722 is configured to receive the first wireless signal 741 and to send an electrical signal to the internal patch antenna 721 via the electrical connection 723. The internal patch antenna 721 is configured to transmit a second wireless signal 742 inside of the container 710 that can be received by the wireless signal receiver 711. The network analyzer 730 can control signals transmitted by the wireless transmitter 740 and determine the differences between the first wireless signal 741 transmitted by the wireless transmitter 740 and the second wireless signal 742 received by the wireless signal receiver 711.

The different testing arrangements shown in FIGS. 7A and 7B are similar, except that the external patch antenna 722 is located at different places on the container 710. In FIG. 7A, the external patch antenna 722 is located in a horizontal position with respect to the wireless transmitter 740. In FIG. 7B, the external patch antenna 722 is located in a vertical position with respect to the wireless transmitter 740.

Figure 7C:
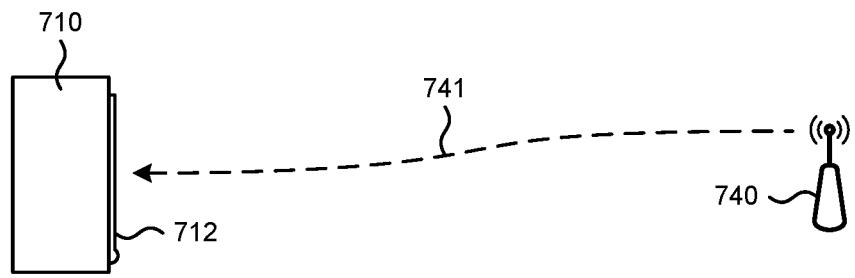
FIGS. 7C to 7E depict possible orientations of the container with respect a wireless transmitter.
Figure 7D:
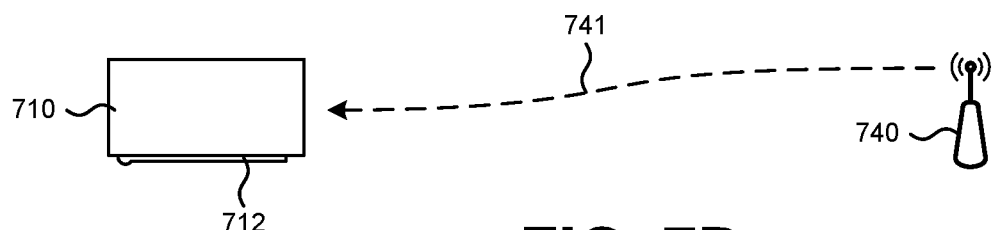
Figure 7E:
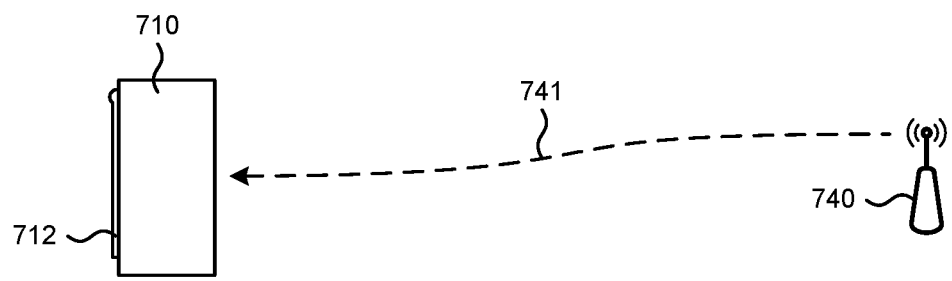

FIGS. 7C to 7E depict possible orientations of the container 710 with respect a wireless transmitter 740. FIGS. 7C to 7E depict overhead views of the container 710, showing a side of the container 710 that includes a door 712. The container 710 can be a metal cabinet and the door 712 can have a metal frame with a plastic or glass window. In the orientation shown in FIG. 7C, the door is facing toward the wireless transmitter 740 (i.e., at an angle of approximately 0° with respect to the wireless transmitter 740). In the orientation shown in FIG. 7D, the door is facing in a direction substantially parallel to the wireless transmitter 740 (i.e., at an angle of approximately 90° with respect to the wireless transmitter 740). In the orientation shown in FIG. 7E, the door is facing away from the wireless transmitter 740 (i.e., at an angle of approximately 180° with respect to the wireless transmitter 740).

Using a variety of orientations depicted in FIGS. 7A to 7E, the effects of having a patch antenna system and the effects of door position were investigated. In a first test, a series of measurements were recorded with and without a patch antenna system on the container 710. This afforded differential measurements comparing the baseline signal strength within the container 710 to the affected signal strength produced by the patch antenna system (when connected). During the testing, the orientation of the door 712 of the container 710 with respect to the wireless transmitter 740 was adjusted. The door 712 included a glass portion which can allow wireless signals to pass with much less attenuation than the metal portions of the container 710. In addition, the orientation of the external patch antenna 722 was adjusted from being in a horizontal position on the container 710 to a vertical position on the container 710. Results from the first test are shown below in Table 1.

TABLE 1

Test results with and with patch antenna system

| Container configuration | Measurement (dB) of wireless signal receiver in container | | |
|---|---|---|---|
| | No patch antenna system | Vertical external antenna | Horizontal external antenna |
| Door at 0° angle | −68 dB | −71 dB | −70 dB |
| Door at 90° angle | −82 dB | −79 dB | −78 dB |
| Door at 180° angle | −92 dB | −81 dB | −84 dB |

In a second test, power provided by the network analyzer 730 when sending signals to the wireless transmitter 740 was adjusted. This permitted any changes in the experimental data due to propagation variations to be detected. Additionally, this provided further supporting data for the first test. The second test was performed with the door 712 of the container 710 facing away from the wireless transmitter 740 (i.e. at a 180° angle) as that was the lowest baseline signal strength from the first test. Results from the second test are shown below in Table 2.

TABLE 2

Test results with and with patch antenna system

| Container configuration | Analyzer-provided power | Measurement (dB) of wireless signal receiver in container | |
|---|---|---|---|
| | | With patch antenna system | No patch antenna system |
| Door at 180° angle | 0 dB | −84 dB | −87 dB |
| Door at 180° angle | 5 dB | −82 dB | −86 dB |
| Door at 180° angle | 10 dB | −83 dB | −86 dB |

As shown in the results of the first and second tests, there was an increase in signal strength between measurements with and without the patch antenna system. The patch antenna system was able to increase the wireless signal field strength inside the container 710 by at least 3 dB in most test configurations and more than 3 dB in some test configurations. A 3 dB gain using a patch antenna system effectively doubles the strength of wireless signals that are sent into and outside of the container 710.

Both of the tests described indicate that various orientations of the container 710 and various placements of the external patch antenna 722 can affect the strength of the signal inside of the container 710. When an internal patch antenna 721 and an external patch antenna 722 are removably mounted by an end user, the end user may not know where a wireless transmitter or receiver is located with respect to the container 710. The end user may also not be able to reposition or reorient the container 710 and the end user may not know the optimal location of the external patch antenna 722 on the container. In this case, the end user may use a trial-and-error method of removably mounting the internal patch antenna 721 and the external patch antenna 722 on the container 710. In this case, the ability to easily remove the internal patch antenna 721 and the external patch antenna 722 and reposition the internal patch antenna 721 and the external patch antenna 722 can greatly aid in the end user's ability to try different positions of the internal patch antenna 721 and the external patch antenna 722 until suitable positions are found.

Figure 8:
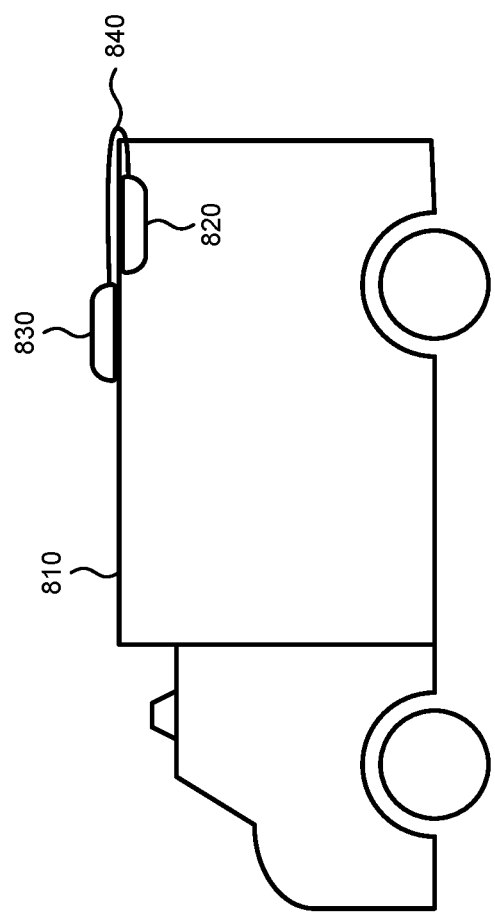
FIG. 8 depicts another type of container that could benefit from the use of a patch antenna system.

FIG. 8 depicts another type of container that could benefit from the use of a patch antenna system. As discussed above, a container for a wirelessly-communicating device can take the form of a cabinet, a storage room, a vehicle trunk, a vehicle compartment, an elevator, a subway compartment, a train compartment, an aircraft compartment, a vehicle, and the like. FIG. 8 depicts a vehicle 810, such as an ambulance, that can include a wirelessly-communicating device. In one example, an AED can be located inside of the vehicle 810 and used to treat a patient that is en route to a hospital. The AED may communicate via a cellular network with the hospital to provide information about the patient and/or treatment by the AED while en route. In such a case, wireless communications between the AED and the cellular network may be difficult due to the enclosed nature of the vehicle 810. To address this issue, a patch antenna system—including an internal patch antenna 820, an external patch antenna 830, and an electrical connection 840 between the internal patch antenna 820 and the external patch antenna 830—to increase signal strengths of wireless signals passed from outside the vehicle 810 to inside the vehicle 810 and vice versa.

While many of the embodiments described herein include a pair of patch antennas, this is not the only pair of antennas that could be used. Any other pair of antennas capable of transmitting and receiving the intended frequencies can be suitable, such as dipole antennas. It is also possible that an internal antenna and an external antenna could be dissimilar antennas. For example, an external antenna could be a dipole antenna when an internal is a patch antenna.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

In general, the various features and processes described above may be used independently of one another, or may be combined in different ways. All possible combinations and subcombinations are intended to fall within the scope of this disclosure. For example, this disclosure includes other combinations and sub-combinations equivalent to: extracting an individual feature from one embodiment and inserting such feature into another embodiment; removing one or more features from an embodiment; or both removing a feature from an embodiment and adding a feature extracted from another embodiment, while providing the advantages of the features incorporated in such combinations and sub-combinations irrespective of other features in relation to which it is described. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example examples. The example systems and components described herein may be configured differently than described. For example, elements may be added to, removed from, or rearranged compared to the disclosed example examples.

While certain example or illustrative examples have been described, these examples have been presented by way of example only, and are not intended to limit the scope of the inventions disclosed herein. Indeed, the novel methods and systems described herein may be embodied in a variety of other forms. The accompanying claims and their equivalents are intended to cover such forms or modifications as would fall within the scope and spirit of certain of the inventions disclosed herein.

I claim:

1. A system comprising:
    a container;
    a device located within the container, the device configured to communicate wireless signals at a plurality of particular frequencies;
    an internal antenna removably mounted to an internal surface of the container, the internal antenna comprising a first ground plane, a first dielectric substrate, and a first patch characterized by a particular shape designed to tune the internal antenna to receive and radiate signals at the plurality of particular frequencies;
    an external antenna removably mounted to an external surface of the container, the external antenna comprising a second ground plane, a second dielectric substrate, and a second patch characterized by a particular shape designed to tune the external antenna to receive and radiate signals at the plurality of particular frequencies; and
    an electrical connection between the internal antenna and the external antenna;
    wherein the system is configured such that the internal antenna is operative to receive a first wireless signal from the device and provide a first electrical signal based on the first wireless signal via the electrical connection to the external antenna, and radiate from the external antenna a second wireless signal based on the first electrical signal;
    wherein the system is further configured such that the external antenna is operative to receive a third wireless signal, provide a second electrical signal based on the third wireless signal via the electrical connection to the internal antenna, and radiate from the internal antenna a fourth wireless signal based on the second electrical signal;
    wherein at least one of the internal and external antennas is formed as a patch antenna;
    wherein the shape of the patch antenna is selected to tune the patch antenna to receive and radiate signals at one or more of the particular frequencies; and
    wherein the patch antenna includes a backplane and a patch that includes first and second slots formed in the patch so as to be parallel to each other.

2. The system of claim 1, wherein the internal antenna is formed as an internal patch antenna and the external antenna is formed as an external patch antenna.

3. The system of claim 2, wherein the plurality of particular frequencies comprise at least one of a cellular network frequency, a Wi-Fi frequency, or an RFID tag frequency.

4. The system of claim 3, wherein the container is constructed of a material that attenuates or blocks wireless signal transmissions.

5. The system of claim 4, wherein the container comprises at least one of a vehicle trunk or compartment.

6. The system of claim 1, wherein the patch further comprises third and fourth slots formed in the patch to be parallel to each other, wherein the third and fourth parallel slots are substantially orthogonal to the first and second slots.

7. The system of claim 6, wherein the patch is formed in two pieces, including a central rectangle and an outer rectangular loop, and wherein the first, second, third, and fourth slots comprise the area between the central rectangle and the outer rectangular loop.

8. A system comprising:
    a container;
    a device located within the container, the device configured to communicate wireless signals at a plurality of particular frequencies;
    an internal antenna removably mounted to an internal surface of the container, the internal antenna comprising a first ground plane, a first dielectric substrate, and a first patch characterized by a particular shape designed to tune the internal antenna to receive and radiate signals at the plurality of particular frequencies;
    an external antenna removably mounted to an external surface of the container, the external antenna comprising a second ground plane, a second dielectric substrate, and a second patch characterized by a particular shape designed to tune the external antenna to receive and radiate signals at the plurality of particular frequencies; and
    an electrical connection between the internal antenna and the external antenna;
    wherein the system is configured such that the internal antenna is operative to receive a first wireless signal from the device and provide a first electrical signal based on the first wireless signal via the electrical connection to the external antenna, and radiate from the external antenna a second wireless signal based on the first electrical signal;
    wherein the system is further configured such that the external antenna is operative to receive a third wireless signal, provide a second electrical signal based on the third wireless signal via the electrical connection to the internal antenna, and radiate from the internal antenna a fourth wireless signal based on the second electrical signal;
    wherein at least one of the internal and external antennas is formed as a patch antenna;
    wherein the shape of the patch antenna is selected to tune the patch antenna to receive and radiate signals at one or more of the particular frequencies; and
    wherein the patch antenna includes a backplane and a patch formed in five pieces, with a central plus-shaped piece and four rectangle pieces in four quadrants of the plus-shaped piece; wherein slots are formed in areas between the plus-shaped piece and the four rectangular pieces.

9. A system comprising:
a container;
a device located within the container, the device configured to communicate wireless signals at a plurality of particular frequencies;
an internal antenna removably mounted to an internal surface of the container, the internal antenna comprising a first ground plane, a first dielectric substrate, and a first patch characterized by a particular shape designed to tune the internal antenna to receive and radiate signals at the plurality of particular frequencies;
an external antenna removably mounted to an external surface of the container, the external antenna comprising a second ground plane, a second dielectric substrate, and a second patch characterized by a particular shape designed to tune the external antenna to receive and radiate signals at the plurality of particular frequencies; and
an electrical connection between the internal antenna and the external antenna;
wherein the system is configured such that the internal antenna is operative to receive a first wireless signal from the device and provide a first electrical signal based on the first wireless signal via the electrical connection to the external antenna, and radiate from the external antenna a second wireless signal based on the first electrical signal;
wherein the system is further configured such that the external antenna is operative to receive a third wireless signal, provide a second electrical signal based on the third wireless signal via the electrical connection to the internal antenna, and radiate from the internal antenna a fourth wireless signal based on the second electrical signal;
wherein at least one of the internal and external antennas is formed as a patch antenna;
wherein the shape of the patch antenna is selected to tune the patch antenna to receive and radiate signals at one or more of the particular frequencies; and
wherein the external antenna is tuned to receive wireless signals having a target carrier frequency of 900 MHz, 1,800 MHz, or 2.4 GHz; and the internal antenna is tuned to transmit wireless signals at the target carrier frequency.

* * * * *